US011890195B1

(12) United States Patent
Wang et al.

(10) Patent No.: US 11,890,195 B1
(45) Date of Patent: Feb. 6, 2024

(54) LEAFLET CAPTURE DEVICE AND SYSTEM, AND ASSEMBLING METHOD

(71) Applicant: SHANGHAI NEWMED MEDICAL CO., LTD, Shanghai (CN)

(72) Inventors: Haishan Wang, Shanghai (CN); Qifeng Yu, Shanghai (CN); Tao Qin, Shanghai (CN)

(73) Assignee: SHANGHAI NEWMED MEDICAL CO., LTD., Shanghai (CN)

( * ) Notice: Subject to any disclaimer, the term of this patent is extended or adjusted under 35 U.S.C. 154(b) by 0 days.

(21) Appl. No.: 18/547,157

(22) PCT Filed: Nov. 18, 2021

(86) PCT No.: PCT/CN2021/131388
§ 371 (c)(1),
(2) Date: Aug. 19, 2023

(87) PCT Pub. No.: WO2022/174635
PCT Pub. Date: Aug. 25, 2022

(30) Foreign Application Priority Data

Feb. 22, 2021 (CN) .......................... 202110199564.2

(51) Int. Cl.
*A61F 2/24* (2006.01)
(52) U.S. Cl.
CPC .................................. *A61F 2/2466* (2013.01)
(58) Field of Classification Search
CPC .... A61F 2/2436; A61F 2/2409; A61F 2/2412; A61F 2/2418; A61F 2/2427; A61F 2/243;
(Continued)

(56) References Cited

U.S. PATENT DOCUMENTS

| 5,586,983 | A  | 12/1996 | Sanders et al. |
| 2014/0379074 | A1 | 12/2014 | Spence et al. |

(Continued)

FOREIGN PATENT DOCUMENTS

| CN | 106604699 A | 4/2017 |
| CN | 106943222 A | 7/2017 |

(Continued)

*Primary Examiner* — Matthew J Lawson
*Assistant Examiner* — Rebecca Lynee Zimmerman
(74) *Attorney, Agent, or Firm* — SALIWANCHIK, LLOYD & EISENSCHENK (57) ABSTRACT

A leaflet capture device and system, and an assembling method. The leaflet capture device comprises: a wire body configured to be spiral and comprising a distal coil, an intermediate coil, and a proximal coil which are arranged in sequence; and a proximal joint comprising a proximal joint main body portion, a proximal clamping jaw, and a proximal clamping portion. The proximal clamping jaw is arranged on one end of the proximal joint main body portion; the proximal clamping portion is arranged on the other end of the proximal joint main body portion; the proximal joint is provided with a proximal through hole passing the proximal clamping jaw through the clamping portion via the proximal joint main body portion; a proximal end portion of the proximal coil is clamped in the proximal clamping jaw after being fixed to the proximal joint main body portion; the proximal through hole is communicated with the proximal end portion of the proximal coil; the proximal clamping portion is fitted to a releasable portion of a delivery device; a pushing member of the delivery device abuts against the proximal end portion of the proximal coil via the proximal through hole. The leaflet capture device can be accurately arranged at a suitable position, so that the difficulty of delivery of a leaflet capture ring is reduced, and the operation time is shortened.

17 Claims, 8 Drawing Sheets

(58) Field of Classification Search
CPC .......... A61F 2/2466; A61F 2/2463; A61F 2002/9528; A61F 2230/0091; A61F 2250/006; A61F 2250/0063; A61B 2017/00243
See application file for complete search history.

(56) References Cited

U.S. PATENT DOCUMENTS

| | | |
|---|---|---|
| 2018/0055630 A1 | 3/2018 | Patel et al. |
| 2018/0177594 A1* | 6/2018 | Patel .......... A61F 2/2427 |
| 2019/0216601 A1 | 7/2019 | Purcell et al. |
| 2020/0107932 A1 | 4/2020 | Rabito et al. |

FOREIGN PATENT DOCUMENTS

| | | |
|---|---|---|
| CN | 109789019 A | 5/2019 |
| CN | 110573113 A | 12/2019 |
| CN | 111467083 A | 7/2020 |
| CN | 111568607 A | 8/2020 |
| CN | 111970993 A | 11/2020 |
| CN | 212308131 U | 1/2021 |
| CN | 215307039 U | 12/2021 |
| CN | 113891695 A | 1/2022 |
| WO | 2018039589 A1 | 3/2018 |
| WO | 2018197721 A1 | 11/2018 |
| WO | 2019164516 A1 | 8/2019 |

* cited by examiner

LEAFLET CAPTURE DEVICE AND SYSTEM, AND ASSEMBLING METHOD

CROSS REFERENCE TO RELATED APPLICATIONS

This application is a National Stage of International Application No. PCT/CN2021/131388, filed on Nov. 18, 2021, which claims priority to Chinese Patent Application No. 202110199564.2, filed on Feb. 22, 2021; both of which are hereby incorporated by reference in their entireties.

TECHNICAL FIELD

The present application relates to the technical field of medical instruments, in particular to a valve leaflet capture device, a valve leaflet capture system and an assembling method thereof.

BACKGROUND ART

Mitral valve diseases are common cardiac valve diseases, and patients with mitral valve diseases are also the largest group in cardiac valve surgery department, accounting for about 60%. Mitral valve interventional therapy provides a good therapeutic solution, and includes transcatheter mitral valve repair and transcatheter mitral valve replacement. Transcatheter mitral valve replacement is the mainstream development direction at present, and countries all over the world have invested heavily in the research and development of transcatheter mitral valve replacement. Transcatheter mitral valve replacement has to face the soft mitral valve leaflets; in addition, with the continuous change of cardiac cycle and condition of disease, the mitral valve leaflets can't provide radial support for the valve stent. At present, such a problem is usually solved by an valve in ring technique.

However, there is a problem with the present valve in ring technique that a valve leaflet catching ring has to be arranged at a proper position around the mitral valve leaflet before an artificial valve is implanted, so as to provide certain supporting force for the mitral valve leaflet, and further provide a radial supporting force for the artificial valve implanted subsequently. However, owing to the complex cardiac structure, the valve leaflet catching ring can't be accurately arranged at an appropriate position, resulting in difficulties in the application of the intra-annular valve technique and heavily time-consuming operation. Therefore, how to accurately arrange the valve leaflet catching ring at an appropriate position to reduce the difficulties in delivery of the valve leaflet catching ring and shorten the operation time has become an urgent technical problem to be solved.

SUMMARY OF THE INVENTION

The object of one or more examples in this specification is to provide a valve leaflet capture device, a valve leaflet capture system and a manufacturing method thereof, in order to accurately arrange the valve leaflet capture device at an appropriate position, reduce the difficulties in delivery of the valve leaflet catching ring and shorten the operation time.

In order to solve the above technical problems, one or more examples in this specification are implemented as follows:

In a first aspect, a valve leaflet capture device is provided, comprising: a wire body configured in a spiral shape, comprising a distal coil, a middle coil and a proximal coil that are sequentially arranged, wherein the distal coil is arranged at a distal end of the wire body, and the proximal coil is arranged at a proximal end of the wire body, wherein both the spiral inner diameter of the proximal coil and the spiral inner diameter of the distal coil are greater than the spiral inner diameter of the middle coil; and a proximal joint, comprising a proximal joint body, a proximal clamping jaw and a proximal clamping portion, wherein the proximal clamping jaw is arranged at one end of the proximal joint body, the proximal clamping portion is arranged at the other end of the proximal joint body, and the proximal joint is provided with a proximal through-hole that runs through the proximal joint body from the proximal clamping portion to the proximal clamping jaw, and the proximal end of the proximal coil is clamped in the proximal clamping jaw after being fixed to the proximal joint body, wherein the proximal through-hole is in communication with the proximal end of the proximal coil, and the proximal clamping portion is configured for clamping a releasable portion of a delivery device, and a pushing member of the delivery device pushes against the proximal end of the proximal coil through the proximal through-hole.

In a second aspect, a valve leaflet capture system is provided, comprising a delivery device and the valve leaflet capture device as described above, wherein the delivery device comprises a pushing member, and the delivery device is provided with a distal releasable portion and a delivery through-hole running through the distal releasable portion, the proximal clamping portion clamps the releasable portion, the delivery through-hole is aligned to the proximal through-hole, and the pushing member abuts against the proximal end of the proximal coil after passing through the delivery through-hole and the proximal through-hole.

In a third aspect, an assembling method for a valve leaflet capture device is provided. The assembling method is applicable to a valve leaflet capture device that comprises a wire body, wherein the wire body comprises a distal coil, a middle coil and a proximal coil that are sequentially arranged, the proximal coil is arranged at the proximal end of the wire body, the distal coil is arranged at the distal end of the wire body, and the material of the proximal joint is shape memory alloy, the method comprises: performing thermoforming treatment on the wire body, so that the wire body is formed into a spiral shape, and both the spiral inner diameter of the proximal coil and the spiral inner diameter of the distal coil are greater than the spiral inner diameter of the middle coil; performing thermoforming treatment on the proximal joint, so that the proximal clamping jaw of the proximal joint is in a close state; placing the proximal joint in ice water, so that the proximal clamping jaw is in an open state; placing the proximal end of the proximal coil inside the proximal clamping jaw, so that a shape memory alloy member in the proximal end of the proximal coil is placed inside the proximal joint body; taking out the proximal joint and the proximal coil from the ice water and keeping them at normal temperature while maintaining the positional relationship between the proximal joint and the proximal coil in the ice water, so that the proximal clamping jaw returns to the close state and the proximal end of the proximal coil is clamped in the proximal clamping jaw; welding the shape memory alloy member to the proximal joint in a way that the proximal through-hole is in communication with the proximal end of the proximal coil; and sleeving a developing ring outside the proximal clamping jaw.

As can be seen from the technical solutions provided in one or more examples of the present specification herein, the valve leaflet capture device provided in this application comprises a wire body and a proximal joint, wherein the wire body is configured in a spiral shape, and the spiral wire body comprises a distal coil, a middle coil and a proximal coil that are sequentially arranged, wherein both the spiral inner diameter of the proximal coil and the spiral inner diameter of the distal coil are greater than the spiral inner diameter of the middle coil. With such a structure, it is convenient for the distal coil to capture the valve leaflet when the valve leaflet capture device is delivered to the periphery of cardiac valve leaflets, and the middle coil is wrapped around the cardiac valve leaflets, and can provide enough radial supporting force for the implanted valve stent; at that point, the proximal coil is stuck at the left atrium side, preventing an accidental situation that the valve leaflet capture device falls into the ventricle under the impact of blood flow before the valve stent is implanted. As the name implies, the distal coil is arranged at the distal end of the wire body, the proximal coil is arranged at the proximal end of the wire body, and the proximal end of the proximal coil is fixed to a proximal joint. The proximal joint comprises a proximal joint body, a proximal clamping jaw and a proximal clamping portion, wherein the proximal clamping jaw is arranged at one end of the proximal joint body, the proximal clamping portion is arranged at the other end of the proximal joint body, the proximal joint is provided with a proximal through-hole that runs through the proximal joint body from the proximal clamping portion to the proximal clamping jaw, and the proximal end of the proximal coil is clamped in the proximal clamping jaw after being fixed to the proximal joint body, wherein the proximal through-hole is in communication with the proximal end of the proximal coil. After the proximal clamping portion clamps the releasable portion of the delivery device, the pushing member of the delivery device pushes against the proximal end of the proximal coil through the proximal through-hole, so that the valve leaflet capture device can be fixed to the delivery device, thereby the valve leaflet capture device can be accurately arranged at an appropriate position, the difficulties in the delivery of the valve leaflet catching ring can be reduced, and the operation time can be shortened.

BRIEF DESCRIPTION OF DRAWINGS

To make one or more examples in this specification or the technical solution in the prior art understood better, the accompanying drawings used in the description of one or more examples or in the prior art will be introduced below briefly. Apparently, the accompanying drawings described below only illustrate some examples described in this specification. Those having ordinary skills in the art can obtain other drawings on the basis of these drawings without expending any creative labor.

1—wire body; 10—distal coil; 11—distal joint; 12—proximal joint; 20—middle coil; 30—proximal coil; 4—cardiac valve leaflet; 13—shape memory alloy member; 130—cross section of the shape memory alloy member; 131—shape memory alloy member on the proximal coil; 132—shape memory alloy member on the middle coil; 133—shape memory alloy member on the distal coil; 5—valve stent; 120—proximal joint body; 121—proximal clamping jaw; 122—proximal clamping portion; 123—proximal through-hole; 1220—proximal clamping body; 1221—proximal clamping groove; 1200—proximal assembly slot; 1210—proximal clamping jaw body; 1211—proximal base body; 1212—proximal bifurcation portion; 1213—first proximal branch; 1215—second proximal branch; 1214—proximal end; 14—proximal sleeve; 140—proximal through-slot; 141—inner cavity of the proximal sleeve; 9—delivery device; 90—releasable portion; 900—releasable clamping groove; 910—releasable clamping body; 91—pushing member; 8—developing ring; 7—cladding layer; 70—PET layer; 71—film layer; 710—mesh metal layer; 711—ePTFE layer; 110—distal joint body; 111—distal clamping jaw; 112—guiding head; 15—distal sleeve; 150—distal through-slot; 151—inner cavity of the distal sleeve; 1100—distal assembly slot; 1110—distal clamping jaw body; 1111—distal base body; 1112—distal bifurcation portion; 1113—first distal branch; 1115—second distal branch; 1114—distal end.

EMBODIMENTS

In order to enable those skilled in the art to understand the technical solutions in this description better, the technical solutions in one or more examples of the description will be described clearly and comprehensively with reference to the accompanying drawings in one or more examples of the description. Apparently, the one or more examples described herein are only some examples of the examples in the description but not all possible examples. Those skilled in the art can obtain all the other examples without expending any creative labor, on the basis of one or more examples provided in the present description; however, all those examples shall be deemed as falling in the scope of protection of this application.

Figure 1:
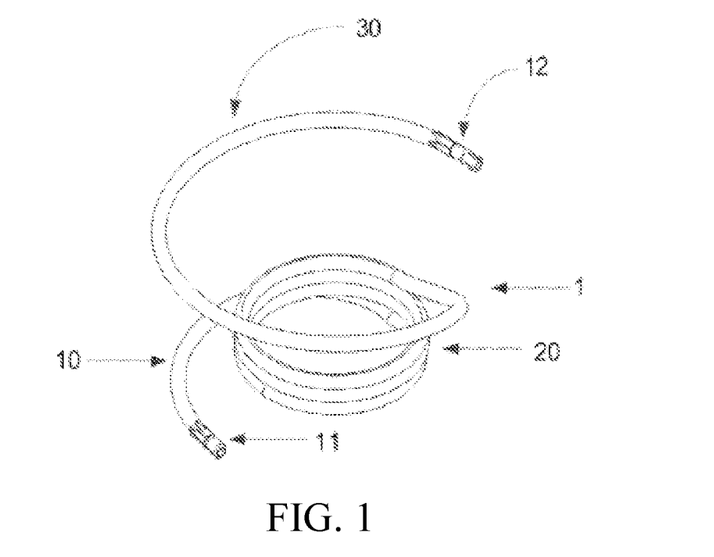
FIG. 1 is a schematic structural diagram of a valve leaflet capture device provided in an example of the present invention.

Please see FIG. 1, which is a schematic diagram of a valve leaflet capture device related to examples of the present invention. It can be seen that the wire body in the valve leaflet capture device provided in the example of the present invention is configured in a spiral shape, the cross section of the wire body may be circular, and the diameter of the wire body may be configured according to the actual physiological structure of the patient's cardiac valve leaflets. It can be seen from the figure that the wire body comprises a distal coil, a middle coil and a proximal coil that are arranged sequentially, and both the spiral inner diameter of the distal coil and the spiral inner diameter of the proximal coil are greater than the spiral inner diameter of the middle coil. In addition, the wire body located at the middle coil accounts for the vast majority of the wire body and is tightly coiled, with a very small gap between the wires. The purpose of such a design is to limit the opening size of the cardiac valve leaflets when the valve leaflet capture device is placed at an appropriate position around the cardiac valve leaflets before a valve stent is implanted in the patient, so that the middle coil will provide a good supporting effect for the valve stent when the valve stent is placed among the valve leaflets. The spiral inner diameter mentioned herein refers to the inner diameter of the spiral coil formed by winding the wire body in a spiral manner.

It should be noted that the proximal end mentioned herein refers to the portion near the operator during the surgical operation, and the distal end mentioned herein refers to the portion away from the operator during the surgical operation.

Example 1

Please see FIG. 1, which is a schematic structural diagram of a valve leaflet capture device provided in an example of the present invention. The valve leaflet capture device comprises a wire body 1 and joints located at two ends of the wire body 1. Here, the joints include a proximal joint 12 and a distal joint 11; as described above, the joint near the operator during the surgical operation is the proximal joint 12, and the joint away from the operator during the surgical operation is the distal joint 11.

As shown in FIG. 1, the wire body 1 is configured in a spiral shape, and comprises a distal coil 10, a middle coil 20 and a proximal coil 30 that are arranged sequentially, wherein the distal coil 10 is arranged at the distal end of the wire body 1, and the proximal coil 30 is arranged at the proximal end of the wire body 1. As shown in FIG. 1, both the spiral inner diameter of the proximal coil 30 and the spiral inner diameter of the distal coil 10 are greater than the spiral inner diameter of the middle coil 20, and the spiral inner diameter of the distal coil 30 varies gradually, as shown in FIG. 1. As described above, with such a structure, it is convenient for the distal coil to capture the valve leaflets as the valve leaflets close up when the valve leaflet capture device is delivered to the periphery of the cardiac valve leaflets. The spiral inner diameter of the distal coil may be set to 30 mm to 40 mm, the arrangement of this size is made so that the opening of the distal coil is large enough to facilitate catching but is not excessively large to avoid abutting against the inner wall of the heart when capturing the valve leaflets. The spiral inner diameter of the middle coil 20 is substantially the same, the adjacent coils in the middle coil 20 are arranged closely, and the middle coil 20 accounts for the vast majority of the wire body 1. When the middle coil 20 is wrapped around the cardiac valve leaflets, it can provide enough radial supporting force for an implanted valve stent; the spiral inner diameter of the proximal coil is slightly larger, so that the proximal coil is stuck at the left atrium side to prevent an accidental situation that the valve leaflet capture device falls into the ventricle under the impact of blood flow before the valve stent is implanted. Therefore, the spiral inner diameter of the proximal coil is slightly larger than the diameter of the mitral annulus. The specific spiral inner diameter of the proximal coil may be set according to the size of the valve annulus of the specific patient, and usually may be 45 mm to 60 mm; this numerical range does not constitute any limitation to the technical solution of this application, and it is understood that the above-mentioned reference numerical range of the spiral inner diameter of the distal coil does not constitute any limitation to the technical solution of this application either.

Figure 2:
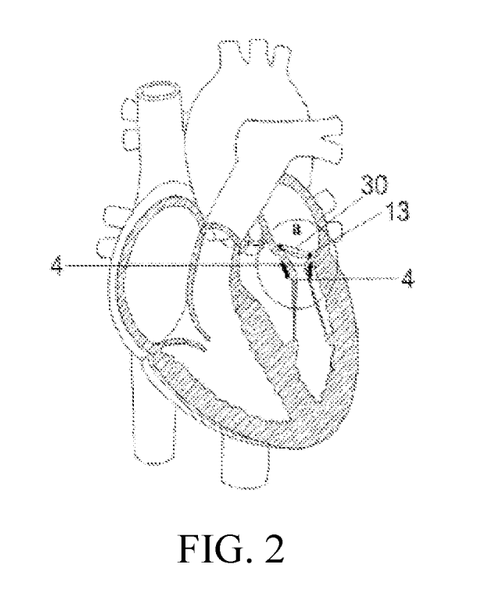
FIG. 2 is a schematic sectional view of the valve leaflet capture device shown in FIG. 1 arranged around cardiac valve leaflets.
Figure 3:
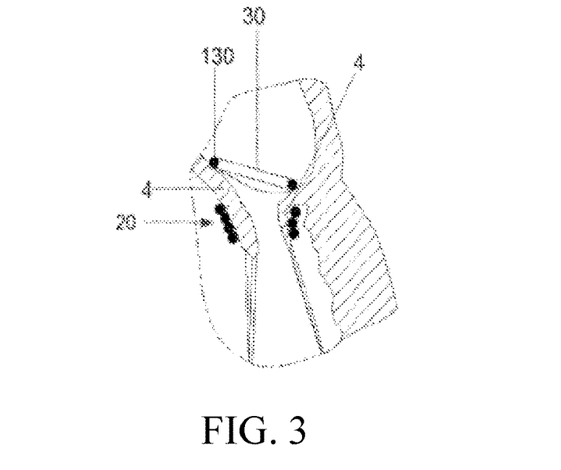
FIG. 3 is a partially enlarged view of a part A of the valve leaflet capture device shown in FIG. 2.
Figure 4:
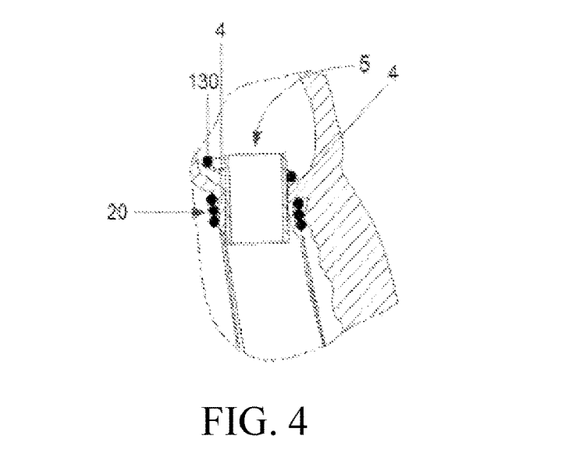
FIG. 4 is a schematic structural diagram of the valve leaflet capture device shown in FIG. 3 after a valve stent is implanted.

As shown in FIGS. 2, 3 and 4, before a valve stent 5 is implanted, a valve leaflet catching ring is arranged around the mitral valve leaflets; especially, in the case that the middle coil is used to reduce the opening size of the mitral valve leaflets before the valve stent 5 is implanted among the mitral valve leaflets, the inner diameter of the valve leaflet catching ring can be smaller than the outer diameter of the expanded valve stent 5. When the valve stent 5 is expanded, it is subject to a radial supporting force exerted by the valve leaflet catching ring, so that the valve stent 5 is not easy to displace axially and the valve stent 5 is reliably fixed. The wire body 1 may include a shape memory alloy member 13, which can provide a supporting force persistently for the valve stent 5, and is beneficial for the patient to be free of the effects caused by valve diseases in a long term. As shown in FIGS. 2, 3 and 4, after the valve leaflet catching ring is arranged around the mitral valve leaflets, the proximal coil 30 is located in the upper left atrium. The black circle in the figures represents the cross section 130 of the shape memory alloy member 13. It can be seen that the adjacent coils of the middle coil 20 is closely arranged when the middle coil 20 is placed at an appropriate position.

Since the shape memory alloy member 13 has been subject to thermoforming treatment at a high temperature, it can be arranged according to the previously thermoformed shape after the wire body 1 is implanted around the cardiac valve leaflets 4.

Figure 5:
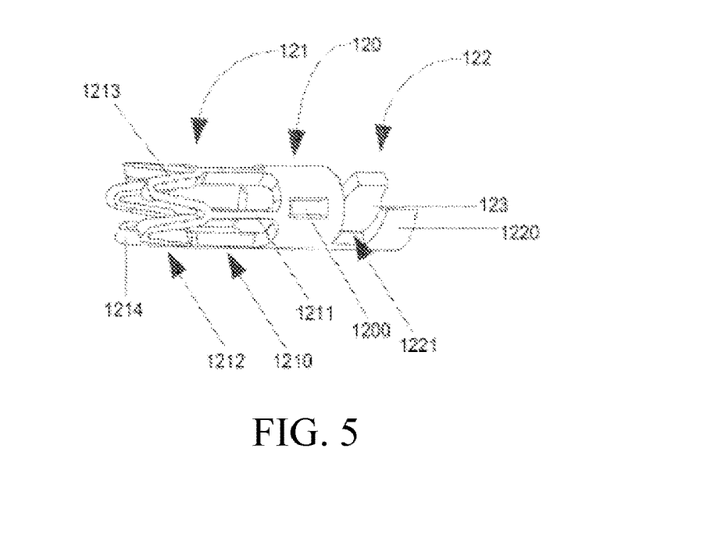
FIG. 5 is a schematic structural diagram of the proximal joint in another valve leaflet capture device provided in an example of the present invention.
Figure 6:
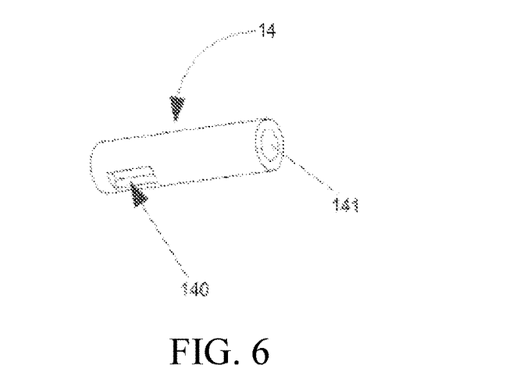
FIG. 6 is a schematic structural diagram of the proximal sleeve in a further another valve leaflet capture device provided in an example of the present invention.
Figure 7:
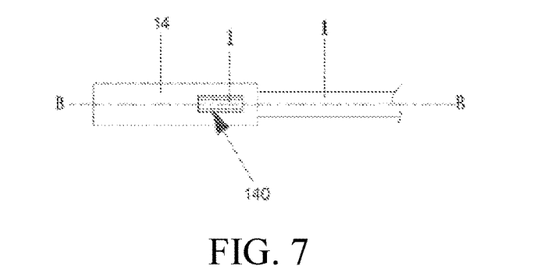
FIG. 7 is a schematic structural view of the valve leaflet capture device shown in FIG. 6 in which the wire body is fixed in the proximal sleeve.
Figure 8:
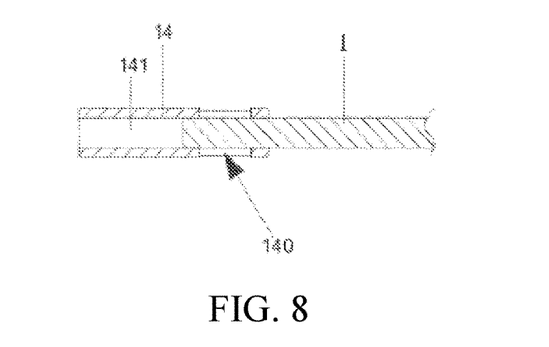
FIG. 8 is a schematic cross-sectional view of the valve leaflet capture device shown in FIG. 7 along a line B-B.

As shown in FIG. 5, the proximal joint 12 comprises a proximal joint body 120, a proximal clamping jaw 121 and a proximal clamping portion 122, wherein the proximal clamping jaw 121 is arranged at one end of the proximal joint body 120, the proximal clamping portion 122 is arranged at the other end of the proximal joint body 120, and the proximal joint 12 is provided with a proximal through-hole 123 that runs from the proximal clamping portion 122 to the proximal clamping jaw 121 through the proximal joint body 120; the proximal end of the proximal coil 30 is clamped in the proximal clamping jaw 121 after being fixed to the proximal joint body 120, with the proximal through-hole 123 in communication with the proximal end of the proximal coil 30; the proximal clamping portion 122 is used for clamping a releasable portion 90 of a delivery device 9 (see FIGS. 12 and 13), and a pushing member 91 of the delivery device 9 pushes against the proximal end of the proximal coil 30 through the proximal through-hole 123. Thus, the valve leaflet capture device is fixed to the delivery device 9, and the pushing member 91 can limit the position of the valve leaflet capture device in the length extension direction of the pushing member 91.

Before the valve leaflet capture device provided in the present invention is delivered, the releasable portion 90 of the delivery device 9 is clamped by the proximal clamping portion 122 of the valve leaflet capture device, and the pushing member 91 is pushed outward on the delivery device 9, so that the pushing member 91 passes through the proximal through-hole 123 and abuts against the proximal end of the proximal coil 30. After the delivery device 9 delivers the valve leaflet capture device to a predetermined position in the human body through a delivery catheter, the pushing member 91 is pulled backward so that the pushing member 912 exits the proximal through-hole 123, and moves the releasable portion 90 with respect to the proximal clamping portion 122 in a direction perpendicular to the length of the pushing member 91, so that the valve leaflet capture device is separated from the delivery device 9.

Figure 21:
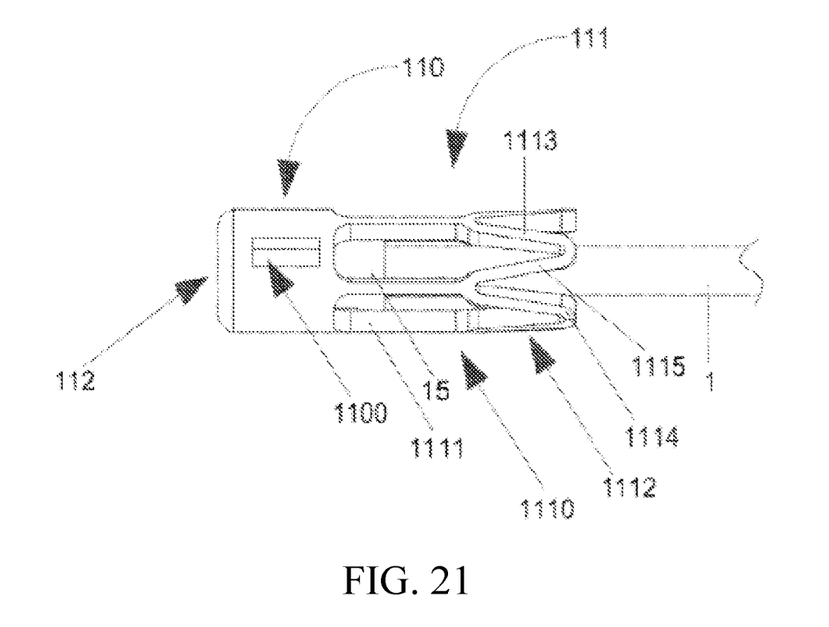
FIG. 21 is a schematic structural view of the valve leaflet capture device shown in FIG. 19 in which the distal sleeve is fixed in the distal joint.

As shown in FIG. 21, in some examples, the valve leaflet capture device provided by this example of the present invention further comprises a distal joint 11, the distal joint 11 comprises a distal joint body 110, a distal clamping jaw 111 and a guiding head 112, wherein the distal clamping jaw 111 is arranged at one end of the distal joint body, the guiding head 112 is arranged at the other end of the distal joint body, and the distal end of the distal coil 10 is clamped in the distal clamping jaw 111 after being fixed to the distal joint body 110.

The outer contour of the guiding head 112 may be rounded, so that the valve leaflet capture device can smoothly bypass human tissues and enter into the interior of the heart after it enters the blood vessels of the human body. The distal clamping jaw 111 and the proximal clamping jaw 121 achieve the same technical effect, i.e., the end of the wire body 1 is clamped firmly after the end of the wire body 1 is fixed to the joint body, thereby the reliability of fixing of the wire body 1 to the joint is improved.

Figure 14:
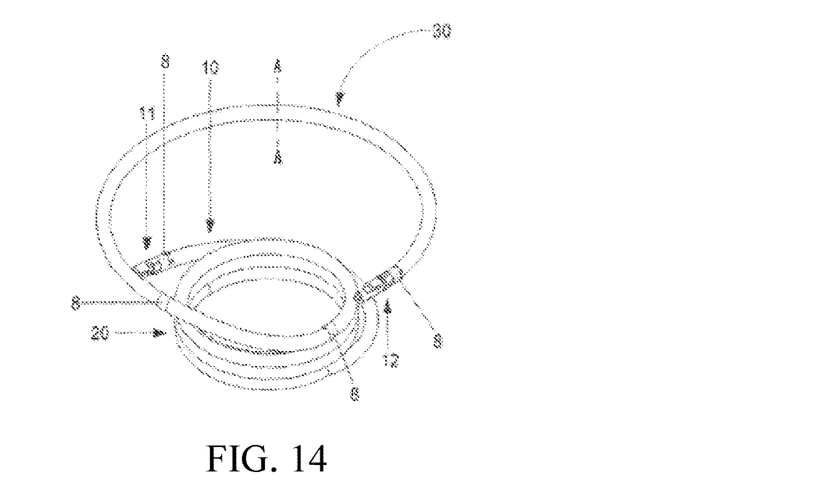
FIG. 14 is a schematic structural diagram of yet another valve leaflet capture device provided in an example of the present invention.
Figure 15:
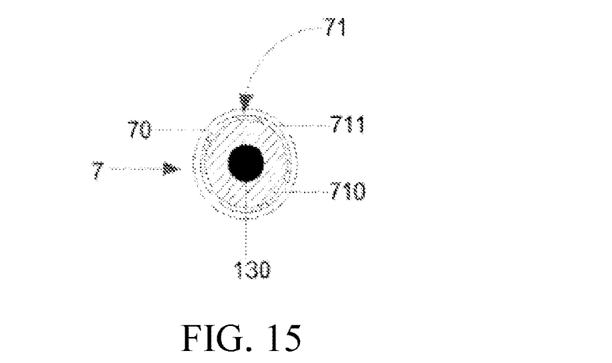
FIG. 15 is a schematic cross-sectional view of the valve leaflet capture device shown in FIG. 14 along a line A-A.

As shown in FIGS. 14 and 15, in some examples, in the valve leaflet capture device provided by this example of the present invention, the wire body 1 comprises a shape memory alloy member 13 extending in the length direction of the wire body 1 and a cladding layer 7 covering the exterior of the shape memory alloy member 13, wherein the distal end of the shape memory alloy member 13 is fixed to the distal joint body 110, the proximal end of the shape memory alloy member 13 is fixed to the proximal joint body 120, and the proximal clamping jaw 121 and the distal clamping jaw 111 are clamped on the cladding layer 7.

It can be seen that after the distal end and the proximal end of the shape memory alloy member 13 are fixed to the distal joint body 110 and the proximal joint body 120, the distal clamping jaw 111 and the proximal clamping jaw 121 are respectively clamped on the cladding layer 7 of the wire body 1. The shape memory alloy member 13 may be a nickel-titanium wire or the like.

Figure 16:
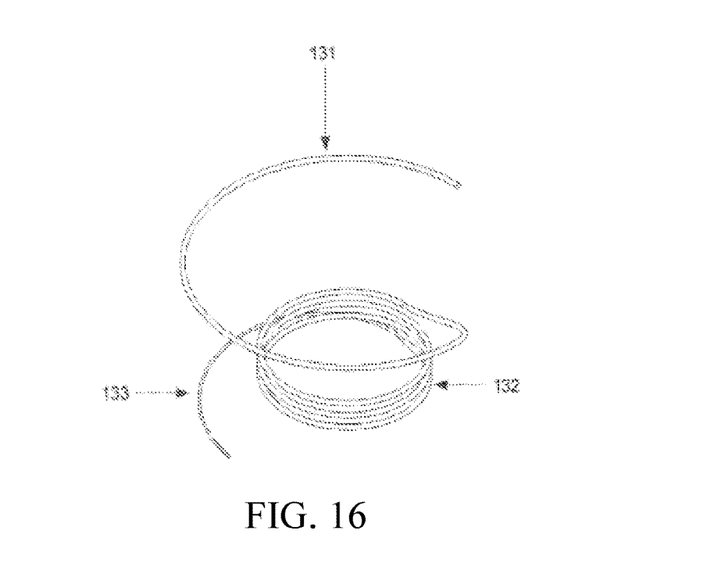
FIG. 16 is a schematic structural diagram of the shape memory alloy member in a further another valve leaflet capture device provided in an example of the present invention.
Figure 17:
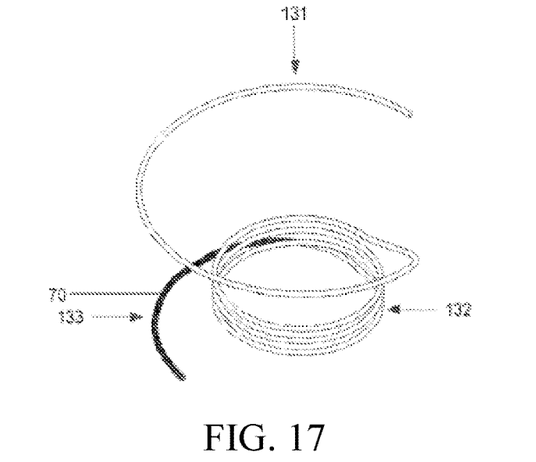
FIG. 17 is a schematic structural diagram of the shape memory alloy member in a further another valve leaflet capture device provided in an example of the present invention.
Figure 18:
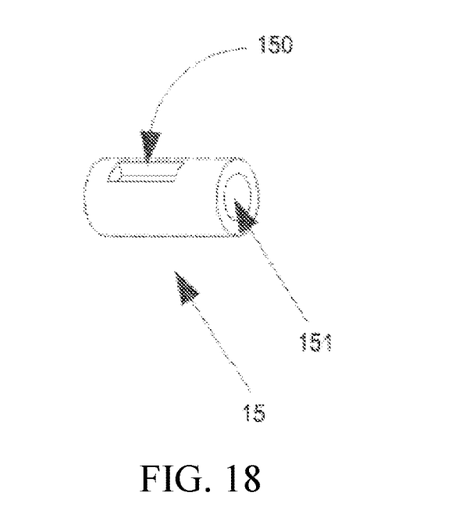
FIG. 18 is a schematic structural diagram of the distal sleeve of the distal joint in yet another valve leaflet capture device provided in an example of the present invention.
Figure 19:
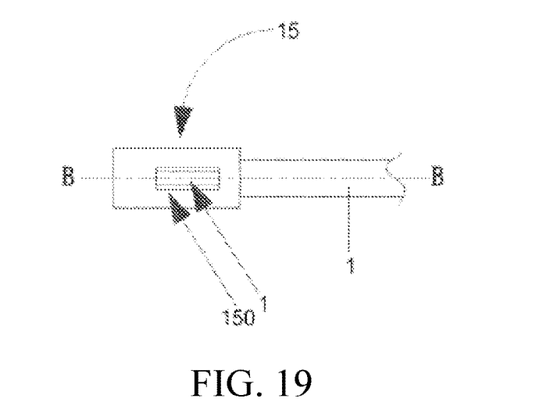
FIG. 19 is a schematic structural view of the valve leaflet capture device shown in FIG. 18 in which the wire body is fixed in the distal sleeve.
Figure 20:
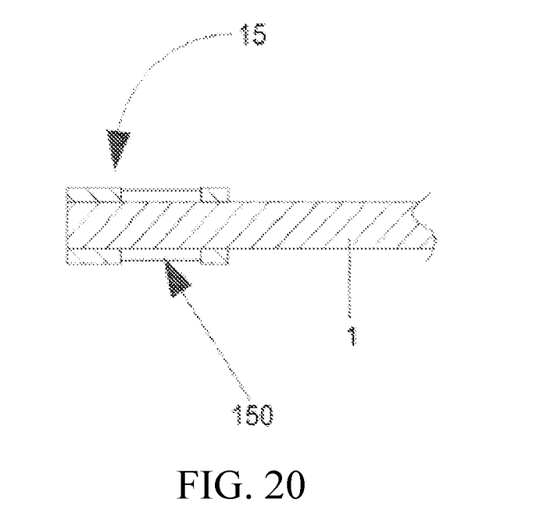
FIG. 20 is a schematic cross-sectional view of the valve leaflet capture device shown in FIG. 19 along a line B-B.

As shown in FIG. 16, in some examples, in the valve leaflet capture device provided by this example of the present invention, the cross-section of the shape memory alloy member 133 located on the distal coil 10 is smaller than the cross-section of the shape memory alloy member 132 located on the middle coil 20 and the cross-section of the shape memory alloy member 131 located on the proximal coil 30, and the cross section 130 of the shape memory alloy member 133 located on the distal coil 10 gradually increases from the distal end of the distal coil 10 to the proximal end of the distal coil 10, till it is equal to the cross section of the shape memory alloy member 132 located on the middle coil 20.

The diameter of the shape memory alloy member 131 located on the proximal coil 30 may be consistent with the diameter of the shape memory alloy member 13 located on the middle coil 20, and is not smaller than 0.7 mm. The diameter of the shape memory alloy member 133 located on the distal coil 10 gradually increases from the distal end of the distal coil 10 to the proximal end of the distal coil 10, so that the distal end of the distal coil 10 has better compliance and can move in blood vessels better. The diameter of distal end of the shape memory alloy member 133 located on the distal coil 10 is not smaller than 0.3 mm, and the maximum diameter of the proximal end of the shape memory alloy member 133 located on the distal coil 10 may be the same as the diameter of the shape memory alloy member 131 located on the proximal coil 30 and the diameter of the shape memory alloy member 132 located on the middle coil 20.

As shown in FIGS. 14 and 15, in some examples, in the valve leaflet capture device provided by this example of the present invention, at least the cladding layer 7 on the distal coil 10 comprises a mesh metal layer 710 and a film layer 71 that are sequentially wrapped outside the shape memory alloy member 13, the ends of the mesh metal layer 710 are fixed to the shape memory alloy member 13, and the cross section of the distal coil 10, the cross section of the middle coil 20 and the cross section of the proximal coil 30 are the same.

The two ends of the mesh metal layer 710 may be welded to the shape memory alloy member 13 respectively, and the mesh metal layer 710 may be woven from circular nickel-titanium wires, stainless steel wires or platinum wires. The mesh metal layer 710 may be provided only on the distal coil 10, or may be provided on the entire wire body 1. If the metal woven layer is provided on the entire wire body 1, it can be ensured that the cross section of the distal coil 10, the cross section of the middle coil 20 and the cross section of the proximal coil 30 are the same. The mesh metal layer 710 may cover the entire wire body 1, and the two ends of the mesh metal layer 710 are welded to the shape memory alloy member 13, thereby the friction between the valve leaflet catching ring and the valve stent 5 is increased.

As shown in FIGS. 14 and 15, in some examples, in the valve leaflet capture device provided by this example of the present invention, the film layer 71 comprises an ePTFE layer 711 and a PET layer 70 that are sequentially wrapped on the mesh metal layer 710, and the PET layer 70 is stitched to the ePTFE layer 711 by means of suture lines, the suture lines run through the mesh metal layer 710. For a coil without a metal woven layer, the ePTFE layer 711 and the PET layer 70 are sequentially wrapped on the shape memory alloy member 13.

To fix the ePTFE layer 711 and the PET layer 70, the suture lines used for stitching the ePTFE layer 711 and the PET layer 70 may run through the gaps of the mesh metal layer 710, so that the suture lines are retained in the mesh metal layer 710, thereby the ePTFE layer 711 and the PET layer 70 can be fixed better. In the case that the cross section of the distal coil 10, the cross section of the middle coil 20 and the cross section of the proximal coil 30 are the same and the mesh metal layer 710 is only provided on the distal coil 10, the foaming process of the ePTFE layer 711 can be accomplished better.

As mentioned above, the proximal clamping jaw 121 and the distal clamping jaw 111 can clamp the two ends of the film layer 71 including the ePTFE layer 711 and the PET layer 70. The cladding layer comprises a mesh metal layer and a film layer that are sequentially wrapped outside the shape memory alloy member, and the film layer comprises an ePTFE layer and a PET layer that are sequentially wrapped outside the mesh metal layer; the proximal end of the ePTFE layer and the proximal end of the PET layer are squeezed into a proximal assembly slot and clamped therein tightly under the pressure of the proximal clamping jaw, and the distal end of the ePTFE layer and the distal end of the PET layer are squeezed into a distal assembly slot and clamped therein tightly under the pressure of the distal clamping jaw.

The ePTFE film material has a microporous structure, with outstanding endothelialization performance, excellent toughness and high biocompatibility. The valve leaflet capture device is straight before it is implanted into the human body. After the valve leaflet capture device is introduced into the heart in the human body, it begins to return to the thermoformed shape as the temperature increases (as shown in FIG. 1), and returns to the spiral shape while catching the valve leaflets. When the two ends of the ePTFE layer 711 are clamped tightly by the distal clamping jaw 111 and the proximal clamping jaw 121, they are subject to axial tension. Therefore, the ePTFE layer 711 must be designed to have at least 7% elongation capability under the working conditions. The effect of clamping the ePTFE layer 711 by means of the distal clamping jaw 111 and the proximal clamping jaw 121 in this application also aims at that feature, i.e., limiting the ePTFE layer 711 that has elongation capability. The ePTFE film layer 71 has a unique structure that is formed by a large number of solid nodes interconnected through a fine fiber matrix. The spacing between the nodes is referred to as inter-distance IND, which is an index of the expansion amount of the ePTFE layer 711. The IND of the ePTFE layer 711 used in the examples of the present invention is 5 μm to 100 μm.

Figure 10:
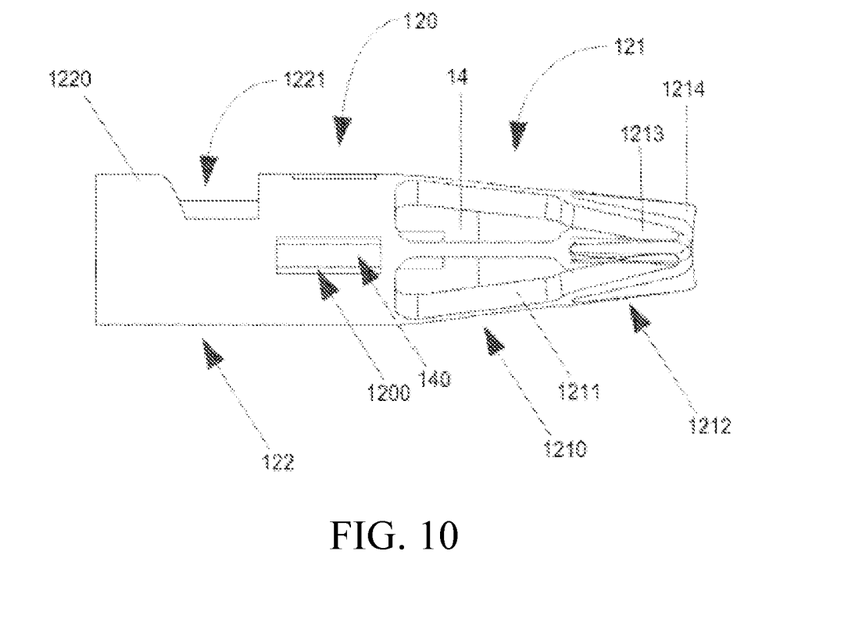
FIG. 10 is a schematic structural diagram of the proximal clamping jaw in a closed state in a further another valve leaflet capture device provided in an example of the present invention.

As shown in FIG. 10, in some examples, in the valve leaflet capture device provided by this example of the present invention, the proximal joint body 120 and the distal joint body 110 are configured in a tubular shape, the proximal clamping jaw 121 closes up towards the axial direction of the proximal joint body 120, and the distal clamping jaw 111 closes up towards the axial direction of the distal joint body 110.

The state of the proximal clamping jaw 121 in FIG. 10 is the state before the valve leaflet capture device is implanted into the heart in the human body, i.e., in that state, the distal end and the proximal end of the wire body 1 can be clamped tightly. During assembly, the ePTFE layer and the PET layer are squeezed into a proximal assembly slot 1200 and clamped therein tightly under the pressure of the proximal clamping jaw.

Figure 12:
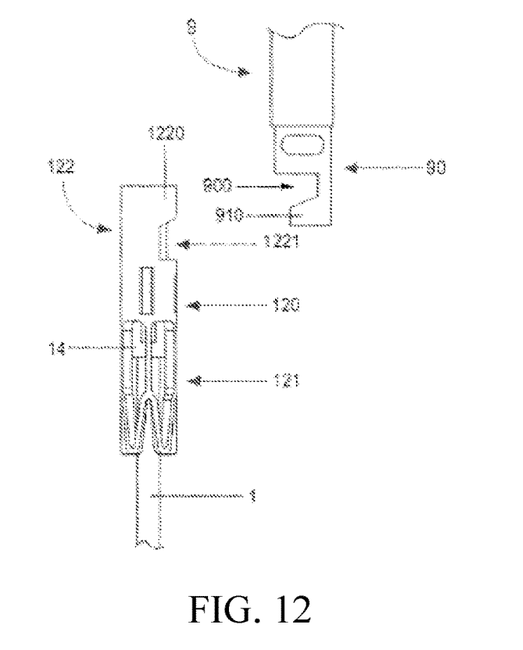
FIG. 12 is a schematic structural diagram illustrating the proximal clamping portion clamping the releasable portion of the delivery device in a further another valve leaflet capture device provided in an example of the present invention.

As shown in FIGS. 5 and 12, in some examples, in the valve leaflet capture device provided by this example of the present invention, the proximal clamping portion 122 comprises a proximal clamping groove 1221 and a proximal clamping body 1220, and a proximal through-hole 123 runs through from the proximal clamping body 1220 to the proximal joint body 120; the proximal clamping body 1220 is integrally formed with the proximal joint body 120, and the proximal clamping groove 1221 is formed by a groove between the proximal clamping body 1220 and the proximal joint body 120, the proximal clamping groove 1221 is used for clamping a releasable clamping groove 900 foamed on the delivery device 9. The valve leaflet capture device is fixed to the delivery device 9 by means of the design of the proximal through-hole 123, the proximal clamping body 1220 and the proximal clamping groove 1221.

In some examples, in the valve leaflet capture device provided by this example of the present invention, as shown in FIGS. 6, 7, 8 and 9, a proximal sleeve 14 is fixed inside the proximal joint body 120, and the distal end of the shape memory alloy member 13 in the wire body 1 is fixed to the interior of a distal sleeve 15. The material of the proximal joint body 120 and the proximal sleeve 14 may be nickel-titanium alloy, and the proximal sleeve 14 may be welded inside the tubular proximal joint body 120 after the shape memory alloy member 13 is welded to the interior of the proximal sleeve 14.

As shown in FIGS. 18, 19, 20 and 21, the distal sleeve 15 is fixed to the interior of the distal joint body 110, the proximal end of the shape memory alloy member 13 is fixed to the interior of the proximal sleeve 14, and the proximal through-hole 123 comprises the inner cavity 141 of the proximal sleeve 14. Likewise, the shape memory alloy member 13 is welded inside the distal sleeve 15, and then the distal sleeve 15 is welded to the interior of the tubular distal joint body 110.

As shown in FIG. 21, in some examples, in the valve leaflet capture device provided by this example of the present invention, the material of the distal joint 11 is shape memory alloy, the side wall of the distal sleeve 15 is provided with a distal through-slot 150, the distal end of the shape memory alloy member 13 is welded to the edges of the distal through-slot 150, the side wall of the distal joint body 110 is provided with a distal assembly slot 1100, and the distal sleeve 15 is at least welded to the edges of the distal assembly slot 1100. The distal through-slot 150 and the distal assembly slot 1100 in the figures facilitate the fixing of the shape memory alloy member 13 to the interior of the distal joint body 110. Alternatively, the shape memory alloy member 13 may be directly welded to the interior of the distal joint body 110; however, with this arrangement, the distal joint body 110 has a smaller inner diameter, accordingly the size of the distal clamping jaw 111 is smaller, and the deformation amount (i.e., closing up and opening) of the distal clamping jaw 111 with a smaller size is smaller; as a result, the distal clamping jaw 111 has a lower biting force, consequently the clamping force of the distal clamping jaw 111 to the end of the wire body 1 is affected.

Figure 9:
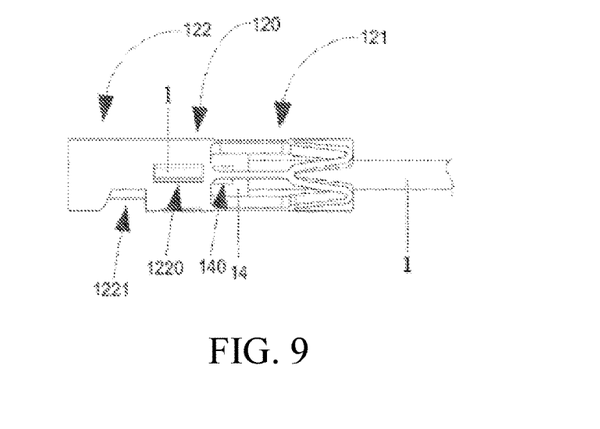
FIG. 9 is a schematic structural view of the valve leaflet capture device shown in FIG. 7 in which the proximal sleeve is fixed in the proximal joint.
Figure 11:
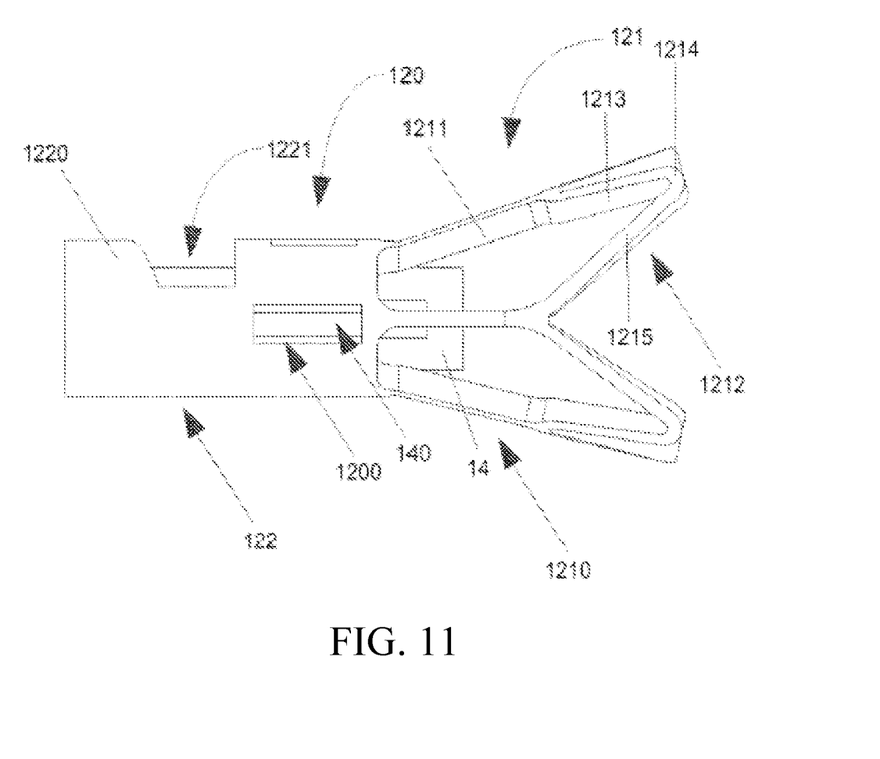
FIG. 11 is a schematic structural diagram of the proximal clamping jaw in an open state in a further another valve leaflet capture device provided in an example of the present invention.

As shown in FIGS. 9, 10 and 11, in some examples, in the valve leaflet capture device provided by this example of the present invention, the material of the proximal joint 12 is shape memory alloy. Likewise, the side wall of the proximal sleeve 14 is provided with a proximal through-slot 140, the proximal end of the shape memory alloy member 13 is welded to the edges of the proximal through-slot 140; the side wall of the proximal joint body 120 is provided with a proximal assembly slot 1200, and the proximal sleeve 14 is at least welded to the edges of the proximal assembly slot 1200. Thus, the clamping force of the proximal clamping jaw 121 to the end of the wire body 1 can be increased under the condition that the shape memory alloy member 13 is firmly fixed to the interior of the proximal joint body 120.

As shown in FIG. 21, in some examples, in the valve leaflet capture device provided by this example of the present invention, at least the proximal clamping jaw 121 and the distal clamping jaw 111 are made of a shape memory alloy material, the distal clamping jaw 111 comprises a plurality of distal clamping jaw bodies 1110 discretely arranged at one end of the distal joint body 110, and the plurality of distal clamping jaw bodies 1110 run from the distal joint body 110 in a direction away from the distal joint body 110 and gradually close together, till the distal ends 1114 of the plurality of distal clamping jaw bodies 1110 are closed together. The distal ends 1114 of the plurality of distal clamping jaws 111 in FIG. 21 are not closed together, while the proximal ends 1214 of the proximal clamping jaws 121 in FIG. 10 are closed together, thereby exert a strong gripping force to the end of the wire body 1.

As shown in FIG. 10, in some examples, in the valve leaflet capture device provided by this example of the present invention, the proximal clamping jaw 121 comprises a plurality of proximal clamping jaw bodies 1210 discretely arranged at one end of the proximal joint body 120, and the plurality of proximal clamping jaw bodies 1210 extend from the proximal joint body 120 in a direction away from the proximal joint body 120 and gradually close together, till the proximal ends 1214 of the plurality of proximal clamping jaw bodies 1210 are closed together.

As shown in FIG. 21, in some examples, in the valve leaflet capture device provided by this example of the present invention, each of the plurality of distal clamping jaw bodies 1110 comprises a distal base body 1111 and a distal bifurcation portion 1112, the distal bifurcation portion 1112 comprises a first distal branch 1113 and a second distal branch 1115, wherein the distal base body 1111 is arranged circumferentially around an orifice of the distal joint body 110, the distal bifurcation portion 1112 extends from the distal base body 1111 in a direction away from the distal joint body 110, and the end of the first distal branch 1113 of each distal clamping jaw body 1110 is connected to the end of the second distal branch 1115 of an adjacent distal clamping jaw body 1110. With such a structure, the clamping force provided by the distal clamping jaw 111 at the distal ends 1114 can be concentrated at one point, thereby the clamping force is great, and the closing effect is excellent, so that the end of the wire body 1 can be reliably clamped. During assembly, the ePTFE layer and the PET layer are squeezed into the distal assembly slot 1100 and clamped tightly therein under the pressure of the distal clamping jaw bodies 1110.

As shown in FIGS. 9, 10 and 11, in some examples, in the valve leaflet capture device provided by this example of the present invention, each of the plurality of proximal clamping jaw bodies 1210 comprises a proximal base body 1211 and a proximal bifurcation portion 1212, the proximal bifurcation portion 1212 comprises a first proximal branch 1213 and a second proximal branch 1215, wherein the proximal base body 1211 is arranged circumferentially around the orifice of the distal joint body 110, the proximal bifurcation portion 1212 extends from the proximal base body 1211 in a direction away from the proximal joint body 120, and the end of the first proximal branch 1213 of each proximal clamping jaw body 1210 is connected to the end of the second proximal branch 1215 of an adjacent proximal clamping jaw body 1210. With such a structure, a good closing effect can be achieved during closing, and an uneven closing phenomenon can be avoided. Since the proximal clamping jaw body 1210 is divided into a proximal base body 1211 and a proximal bifurcation portion 1212, the proximal bifurcation portion 1212 can be opened to a greater angle to facilitate the installation of the wire body 1 when the proximal clamping jaw body 1210 is opened as shown in FIG. 11. The proximal bifurcation portion 1212 can exert a greater clamping force at the proximal ends 1214 so that the end of the wire body 1 can be clamped reliably when the proximal clamping jaw bodies 1210 are closed together as shown in FIG. 10.

As shown in FIG. 14, in some examples, the valve leaflet capture device provided by this example of the present invention further comprises a developing ring 8, the developing ring 8 is sleeved outside the middle coil 20, the distal bifurcation portion 1112 and the proximal bifurcation portion 1212. By arranging the developing ring 8 at the distal bifurcation portion 1112 and the proximal bifurcation portion 1212, on one hand, the position of the developing ring 8 can be acquired for the surgical operator to use as a reference; and on the other hand, the developing ring 8 can clamp the distal bifurcation portion 1112 and the proximal bifurcation portion 1212, so as to improve the clamping force of the distal bifurcation portion 1112 and the proximal bifurcation portion 1212 on the ePTFE layer 711 and the PET layer 70.

With the above technical solution, the valve leaflet capture device provided in this application comprises a wire body and a proximal joint, wherein the wire body is configured in a spiral shape, and the spiral wire body comprises a distal coil, a middle coil and a proximal coil that are sequentially arranged, wherein both the spiral inner diameter of the proximal coil and the spiral inner diameter of the distal coil are greater than the spiral inner diameter of the middle coil. With such a structure, it is convenient for the distal coil to capture the valve leaflet when the valve leaflet capture device is delivered to the periphery of cardiac valve leaflets, and the middle coil is wrapped around the cardiac valve leaflets, and can provide enough radial supporting force for the implanted valve stent; at that point, the proximal coil is stuck at the left atrium side, preventing an accidental situation that the valve leaflet capture device falls into the ventricle under the impact of blood flow before the valve stent is implanted. As the name implies, the distal coil is arranged at the distal end of the wire body, the proximal coil is arranged at the proximal end of the wire body, and the proximal end of the proximal coil is fixed to a proximal joint. The proximal joint comprises a proximal joint body, a proximal clamping jaw and a proximal clamping portion, wherein the proximal clamping jaw is arranged at one end of the proximal joint body, the proximal clamping portion is arranged at the other end of the proximal joint body, the proximal joint is provided with a proximal through-hole that runs through the proximal joint body from the proximal clamping portion to the proximal clamping jaw, and the proximal end of the proximal coil is clamped in the proximal clamping jaw after being fixed to the proximal joint body, wherein the proximal through-hole is in communication with the proximal end of the proximal coil. After the proximal clamping portion clamps the releasable portion of the delivery device, the pushing member of the delivery device pushes against the proximal end of the proximal coil through the proximal through-hole, so that the valve leaflet capture device can be fixed to the delivery device, thereby the valve leaflet capture device can be accurately arranged at an appropriate position, the difficulties in the delivery of the valve leaflet catching ring can be reduced, and the operation time can be shortened.

Example 2

Figure 13:
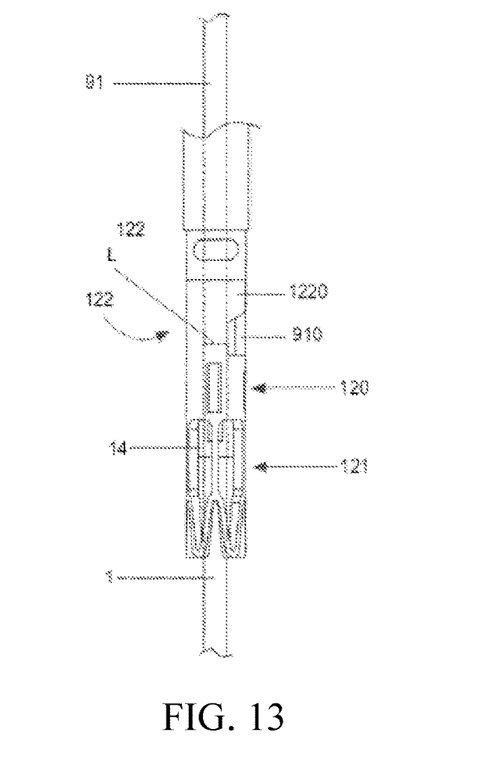
FIG. 13 is a schematic structural diagram of the valve leaflet capture device shown in FIG. 12 after the proximal clamping portion clamps the releasable clamping portion of the delivery device.

Please see in FIGS. 12 and 13, which are schematic structural diagrams of a valve leaflet capture system provided in an example of the present invention. The valve leaflet capture system comprises: a delivery device 9 and the valve leaflet capture device as described above, wherein the delivery device 9 comprises a pushing member 91, and is provided with a releasable portion 90 and a delivery through-hole penetrating the releasable portion 90; the proximal clamping portion 122 clamps the releasable portion 90, the delivery through-hole is aligned to the proximal through-hole 123, and the pushing member 91 is pushed against the proximal end of the proximal coil after it passes through the delivery through-hole and the proximal through-hole 123.

Before the valve leaflet capture device provided in the present invention is delivered, the releasable clamping groove 900 of the releasable portion 90 is in a clamping connection with the proximal clamping body 1220 of the valve leaflet capture device, the releasable clamping body 910 of the releasable portion 90 is in a clamping connection with the proximal clamping groove 1221 of the leaflet capture device, and the delivery device 9 pushes the pushing member 91 outward so that the pushing member 91 passes through the delivery through-hole and the proximal through-hole, thereby the pushing member 91 pushes against the proximal end of the wire body. After the valve leaflet capture device is delivered to a predetermined position in the human body, the pushing member 91 is pulled backward so that the pushing member 91 exits the proximal through-hole, and the valve leaflet capture device is separated from the delivery device 9.

With the above technical solution, the valve leaflet capture device provided in this application comprises a wire body and a proximal joint, wherein the wire body is configured in a spiral shape, and the spiral wire body comprises a distal coil, a middle coil and a proximal coil that are sequentially arranged, wherein both the spiral inner diameter of the proximal coil and the spiral inner diameter of the distal coil are greater than the spiral inner diameter of the middle coil. With such a structure, it is convenient for the distal coil to capture the valve leaflet when the valve leaflet capture device is delivered to the periphery of cardiac valve leaflets, and the middle coil is wrapped around the cardiac valve leaflets, and can provide enough radial supporting force for the implanted valve stent; at that point, the proximal coil is stuck at the left atrium side, preventing an accidental situation that the valve leaflet capture device falls into the ventricle under the impact of blood flow before the valve stent is implanted. As the name implies, the distal coil is arranged at the distal end of the wire body, the proximal coil is arranged at the proximal end of the wire body, and the proximal end of the proximal coil is fixed to a proximal joint. The proximal joint comprises a proximal joint body, a proximal clamping jaw and a proximal clamping portion, wherein the proximal clamping jaw is arranged at one end of the proximal joint body, the proximal clamping portion is arranged at the other end of the proximal joint body, the proximal joint is provided with a proximal through-hole that runs through the proximal joint body from the proximal clamping portion to the proximal clamping jaw, and the proximal end of the proximal coil is clamped in the proximal clamping jaw after being fixed to the proximal joint body, wherein the proximal through-hole is in communication with the proximal end of the proximal coil. After the proximal clamping portion clamps the releasable portion of the delivery device, the pushing member of the delivery device pushes against the proximal end of the proximal coil through the proximal through-hole, so that the valve leaflet capture device can be fixed to the delivery device, thereby the valve leaflet capture device can be accurately arranged at an appropriate position, the difficulties in the delivery of the valve leaflet catching ring can be reduced, and the operation time can be shortened.

Example 3

The steps of an assembling method for the valve leaflet capture device in an example are provided in this example of the present invention. The assembling method for the valve leaflet capture device is applicable to a valve leaflet capture device that comprises a wire body, wherein the wire body comprises a distal coil, a middle coil and a proximal coil that are sequentially arranged, the proximal coil is arranged at the proximal end of the wire body, the distal coil is arranged at the distal end of the wire body, and the material of the proximal joint is shape memory alloy, the assembling method for the valve leaflet capture device provided by this example of the present invention comprises:

Step 10: performing thermoforming treatment on the wire body, so that the wire body is formed into a spiral shape, and both the spiral inner diameter of the proximal coil and the spiral inner diameter of the distal coil are greater than the spiral inner diameter of the middle coil;

As mentioned above, after the valve leaflet capture device is implanted into the heart in the human body, the thermoformed wire body can return to the thermoformed shape, which is beneficial to catching the valve leaflets and providing a strong supporting force for the valve stent subsequently.

Step 20: performing thermoforming treatment on the proximal joint, so that the proximal clamping jaw of the proximal joint is in a close state;

Both the proximal joint and the distal joint are thermoformed at a high temperature, so that the proximal clamping jaw of the proximal joint and the distal clamping jaw of the distal joint are in a closed state (see FIG. 10). In that way, after the valve leaflet capture device is implanted into the human body, the proximal clamping jaw and the distal clamping jaw are kept in a closed state.

Step 30: placing the proximal joint in ice water so as to keep the proximal clamping jaw in an open state;

During assembly, the proximal joint and the distal joint are placed in ice water, and the proximal joint, the distal joint, the proximal clamping jaw and the distal clamping jaw are in an open state in the ice water, as shown in FIG. 11.

Step 40: placing the proximal end of the proximal coil inside the proximal clamping jaw, so that a shape memory alloy member in the proximal end of the proximal coil is placed inside the proximal joint body;

Here, only the assembly of the proximal joint and the wire body is described as an example, and the shape memory alloy member is made of a nickel-titanium wire. The description here may be used as a reference for the distal joint. On one hand, a proximal sleeve to which the proximal end of a nickel-titanium wire is welded is placed inside the proximal joint body; and on the other hand, the ePTFE layer and the PET layer are squeezed into the proximal clamping jaw.

Step 50: taking out the proximal joint and the proximal coil from the ice water while maintaining the positional relationship between the proximal joint and the proximal coil in the ice water and keeping them at normal temperature, so that the proximal clamping jaw returns to the close state and the proximal end of the proximal coil is clamped in the proximal clamping jaw;

Taking out the proximal joint and the proximal coil from the ice water while maintaining the positional relationship between the proximal joint and the proximal coil in the ice water and keeping them at normal temperature. As the temperature increases, the proximal clamping jaw begins to return to the thermoformed closed state; at that point, the ePTFE layer and the PET layer are squeezed into the proximal assembly slot 1200 and/or the distal assembly slot 1100 and are clamped therein under the pressure of the proximal clamping jaw.

Step 60: welding the shape memory alloy member to the proximal joint in a way that the proximal through-hole is in communication with the proximal end of the proximal coil;

Welding the nickel titanium wire inside the proximal joint. If there is a proximal sleeve, only the proximal sleeve has to be welded inside the proximal joint body, and the proximal through-hole is arranged in communication with the proximal end of the proximal coil, so as to ensure that the pushing member can push against the proximal end of the proximal coil subsequently.

Step 70: sleeving a developing ring outside the proximal clamping jaw.

Then the developing ring is sleeved outside the proximal clamping jaw, to effectively prevent the proximal clamping jaw from being opened under the action of other external forces.

With the above technical solution, the valve leaflet capture device provided in this application comprises a wire body and a proximal joint, wherein the wire body is configured in a spiral shape, and the spiral wire body comprises a distal coil, a middle coil and a proximal coil that are sequentially arranged, wherein both the spiral inner diameter of the proximal coil and the spiral inner diameter of the distal coil are greater than the spiral inner diameter of the middle coil. With such a structure, it is convenient for the distal coil to capture the valve leaflet when the valve leaflet capture device is delivered to the periphery of cardiac valve leaflets, and the middle coil is wrapped around the cardiac valve leaflets, and can provide enough radial supporting force for the implanted valve stent; at that point, the proximal coil is stuck at the left atrium side, preventing an accidental situation that the valve leaflet capture device falls into the ventricle under the impact of blood flow before the valve stent is implanted. As the name implies, the distal coil is arranged at the distal end of the wire body, the proximal coil is arranged at the proximal end of the wire body, and the proximal end of the proximal coil is fixed to a proximal joint. The proximal joint comprises a proximal joint body, a proximal clamping jaw and a proximal clamping portion, wherein the proximal clamping jaw is arranged at one end of the proximal joint body, the proximal clamping portion is arranged at the other end of the proximal joint body, the proximal joint is provided with a proximal through-hole that runs through the proximal joint body from the proximal clamping portion to the proximal clamping jaw, and the proximal end of the proximal coil is clamped in the proximal clamping jaw after being fixed to the proximal joint body, wherein the proximal through-hole is in communication with the proximal end of the proximal coil. After the proximal clamping portion clamps the releasable portion of the delivery device, the pushing member of the delivery device pushes against the proximal end of the proximal coil through the proximal through-hole, so that the valve leaflet capture device can be fixed to the delivery device, thereby the valve leaflet capture device can be accurately arranged at an appropriate position, the difficulties in the delivery of the valve leaflet catching ring can be reduced, and the operation time can be shortened.

In summary, while some preferred examples are described above in this specification, those examples are not used to limit the scope of protection of this specification. Any modification, equivalent replacement, or improvement made without departing from the spirit and the principle of this specification shall be deemed as falling in the scope of protection of this specification.

Moreover, it should also be noted that the terms "comprise", "include" or any other variant thereof are intended to encompass non-exclusive inclusion, such that a process, method, product or device comprising a plurality of elements includes not only those elements but also other elements not listed explicitly herein, or further includes elements that are inherent to such a process, method, product or device. An element defined by the phrase "comprising a . . . " does not exclude the presence of additional identical elements in the process, method, product or device including the element, provided that there is no more limitations.

The examples in this specification are described in a progressive way, the individual examples can serve as references for each other for identical or similar parts among the examples, and each example focuses on the differences from the other examples. Especially, the system examples are described in a relatively simple way since they are essentially similar to the method examples, reference may be made to the relevant description in the method examples for the system examples.

Some specific examples are described above in this specification. Other examples are also within the scope of the appended claims. In some cases, the actions or steps mentioned in the claims may be performed in an order different from that in the examples and still can achieve the desired results. In addition, the processes depicted in the accompanying drawings may not necessarily require the illustrated specific order or sequential order to achieve the desired results. In some examples, multi-task processing and parallel processing are also possible or may be advantageous.

The invention claimed is:

1. A valve leaflet capture device, comprising:
   a wire body, configured in a spiral shape, comprising a distal coil, a middle coil and a proximal coil that are sequentially arranged, wherein the distal coil is arranged at a distal end of the wire body, and the proximal coil is arranged at a proximal end of the wire body, wherein both a spiral inner diameter of the proximal coil and a spiral inner diameter of the distal coil are greater than a spiral inner diameter of the middle coil; and
   a proximal joint, comprising a proximal joint body, a proximal clamping jaw and a proximal clamping portion, wherein the proximal clamping jaw is arranged at one end of the proximal joint body, the proximal clamping portion is arranged at an other end of the proximal joint body, and the proximal joint is provided with a proximal through-hole that runs through the proximal joint body from the proximal clamping portion to the proximal clamping jaw, and a proximal end of the proximal coil is clamped in the proximal clamping jaw after being fixed to the proximal joint body, the proximal clamping jaw is configured to tightly clamp the proximal end of the wire body after fixing the proximal end of the wire body to the joint body, the proximal through-hole is in communication with the proximal end of the proximal coil, and the proximal clamping portion is configured for clamping a releasable portion of a delivery device, and a pushing member of the delivery device pushes against the proximal end of the proximal coil through the proximal through-hole.

2. The valve leaflet capture device according to claim 1, further comprising a distal joint, the distal joint comprises a distal joint body, a distal clamping jaw and a guiding head, wherein the distal clamping jaw is arranged at one end of the distal joint body, the guiding head is arranged at an other end of the distal joint body, and a distal end of the distal coil is clamped in the distal clamping jaw after being fixed to the distal joint body.

3. The valve leaflet capture device according to claim 2, wherein the wire body comprises a shape memory alloy member extending in a length direction of the wire body and a cladding layer covering an exterior of the shape memory alloy member, wherein a distal end of the shape memory alloy member is fixed to the distal joint body, a proximal end of the shape memory alloy member is fixed to the proximal joint body, and the proximal clamping jaw and the distal clamping jaw are clamped on the cladding layer.

4. The valve leaflet capture device according to claim 3, wherein a cross section of the shape memory alloy member on the distal coil gradually increases from the distal end of the distal coil to a proximal end of the distal coil till it is consistent with a cross section of the shape memory alloy member on the middle coil, while a cross-section of the shape memory alloy member on the proximal coil is consistent with the cross section of the shape memory alloy member on the middle coil.

5. The valve leaflet capture device according to claim 3, wherein the cladding layer comprises a mesh metal layer and a film layer that are sequentially wrapped outside the shape memory alloy member, ends of the mesh metal layer are fixed to the shape memory alloy member, and a cross section of the distal coil, a cross section of the middle coil and a cross section of the proximal coil are the same.

6. The valve leaflet capture device according to claim 5, wherein the film layer comprises an ePTFE layer and a PET layer that are sequentially wrapped outside the mesh metal layer, and the PET layer is stitched to the ePTFE layer by means of suture lines, the suture lines run through the mesh metal layer.

7. The valve leaflet capture device according to claim 6, wherein the proximal joint body and the distal joint body are configured in a tubular shape, and the proximal clamping jaw closes together toward an axial direction of the proximal joint body and the distal clamping jaw closes together toward an axis of the distal joint body.

8. The valve leaflet capture device according to claim 7, wherein the proximal clamping portion comprises a proximal clamping groove and a proximal clamping body, the proximal through-hole runs through the proximal clamping body to the proximal joint body, the proximal clamping body is integrally formed with the proximal joint body, and the proximal clamping groove is formed by a groove between the proximal clamping body and the proximal joint body for clamping a releasable clamping groove formed on the delivery device.

9. The valve leaflet capture device according to claim 8, wherein a proximal sleeve is fixed inside the proximal joint body, a distal sleeve is fixed to an interior of the distal joint body, the distal end of the shape memory alloy member in the wire body is fixed to an interior of the distal sleeve, the proximal end of the shape memory alloy member is fixed to an interior of the proximal sleeve, and the proximal through-hole comprises an inner cavity of the proximal sleeve.

10. The valve leaflet capture device according to claim 9, wherein a material of the proximal joint and a material of the distal joint are shape memory alloy, a side wall of the distal sleeve is provided with a distal through-slot, the distal end of the shape memory alloy member is welded to edges of the distal through-slot, a side wall of the distal joint body is provided with a distal assembly slot, and the distal sleeve is at least welded to edges of the distal assembly slot; and/or a side wall of the proximal sleeve is provided with a proximal through-slot, the proximal end of the shape memory alloy member is welded to edges of the proximal through-slot, a side wall of the proximal joint body is provided with a proximal assembly slot, and the proximal sleeve is at least welded to edges of the proximal assembly slot.

11. The valve leaflet capture device according to claim 10, wherein a proximal end of the ePTFE layer and a proximal end of the PET layer are squeezed into the proximal assembly slot and clamped therein firmly under the pressure of the proximal clamping jaw, and/or a distal end of the ePTFE layer and a distal end of the PET layer are squeezed into the distal assembly slot and clamped therein firmly under the pressure of the distal clamping jaw.

12. The valve leaflet capture device according to claim 8, wherein at least the proximal clamping jaw and the distal clamping jaw are made of a shape memory alloy material, the distal clamping jaw comprises a plurality of distal clamping jaw bodies discretely arranged at one end of the distal joint body, and the plurality of distal clamping jaw bodies extend from the distal joint body in a direction away from the distal joint body and gradually close together till distal ends of the plurality of distal clamping jaw bodies are closed together; and/or the proximal clamping jaw comprises a plurality of proximal clamping jaw bodies discretely arranged at one end of the proximal joint body, and the plurality of proximal clamping jaw bodies extend from the proximal joint body in a direction away from the proximal joint body and gradually close together till the proximal ends of the plurality of proximal clamping jaw bodies are closed together.

13. The valve leaflet capture device according to claim 12, wherein each of the plurality of distal clamping jaw bodies comprises a distal base body and a distal bifurcation portion, the distal bifurcation portion comprises a first distal branch and a second distal branch, wherein the distal base body is arranged circumferentially around an orifice of the distal joint body, the distal bifurcation portion extends from the distal base body in a direction away from the distal joint body, and an end of the first distal branch of each distal clamping jaw body is connected to an end of the second distal branch of an adjacent distal clamping jaw body; and/or each of the plurality of proximal clamping jaw bodies comprises a proximal base body and a proximal bifurcation portion, the proximal bifurcation portion comprises a first proximal branch and a second proximal branch, wherein the proximal base body is arranged circumferentially around the orifice of the distal joint body, the proximal bifurcation portion extends from the proximal base body in a direction away from the proximal joint body, and an end of the first proximal branch of each proximal clamping jaw body is connected to an end of the second proximal branch of an adjacent proximal clamping jaw body.

14. The valve leaflet capture device according to claim 13, further comprising a developing ring, which is sleeved outside the middle coil, outside the distal bifurcation portion and outside the proximal bifurcation portion.

15. A valve leaflet capture system, comprising a delivery device and the valve leaflet capture device according to claim 1, wherein the delivery device comprises a pushing member, and is provided with a releasable portion and a delivery through-hole running through the releasable portion, the proximal clamping portion clamps the releasable portion, the delivery through-hole is aligned to the proximal through-hole, and the pushing member abuts against the proximal end of the proximal coil after passing through the delivery through-hole and the proximal through-hole.

16. An assembling method for a valve leaflet capture device, applicable to a valve leaflet capture device that comprises a wire body and a proximal joint, wherein the wire body comprises a distal coil, a middle coil, and a proximal coil that are sequentially arranged, the proximal coil is arranged at a proximal end of the wire body, the distal coil is arranged at a distal end of the wire body, the proximal joint comprises a proximal joint body, a proximal clamping jaw, and a proximal clamping portion, and a material of the proximal joint is shape memory alloy material, the assembling method comprises:

performing thermoforming treatment on the wire body, so that the wire body is formed into a spiral shape, and both a spiral inner diameter of the proximal coil and a spiral inner diameter of the distal coil are greater than a spiral inner diameter of the middle coil;

performing thermoforming treatment on the proximal joint, so that the proximal clamping jaw of the proximal joint is in a close state;

placing the proximal joint in ice water, so that the proximal clamping jaw is in an open state;

placing a proximal end of the proximal coil inside the proximal clamping jaw, so that a shape memory alloy member in the proximal end of the proximal coil is placed inside the proximal joint body;

taking out the proximal joint and the proximal coil from the ice water while maintaining a positional relationship between the proximal joint and the proximal coil in the ice water and keeping them at a normal temperature, so that the proximal clamping jaw returns to the close state and the proximal end of the proximal coil is clamped in the proximal clamping jaw;

welding the shape memory alloy member to a proximal connector in a way that a proximal through-hole is in communication with the proximal end of the proximal coil; and sleeving a developing ring outside the proximal clamping jaw.

17. The assembling method according to claim 16, wherein the proximal joint body is in a tubular shape, and the operation of welding the shape memory alloy member to the proximal joint in a way that the proximal through-hole is in communication with the proximal end of the proximal coil further comprises:

welding the shape memory alloy member to an interior of a proximal sleeve;

sleeving the proximal sleeve inside the proximal joint body; and welding the proximal sleeve to the proximal joint body in a way that the proximal sleeve is coaxially with the proximal joint body, so that an inner cavity of the proximal sleeve serves as a section of the proximal through-hole.

* * * * *